(12) United States Patent
Mitsui

(10) Patent No.: US 11,203,789 B2
(45) Date of Patent: Dec. 21, 2021

(54) **METHOD AND KIT FOR DETECTING BACTERIUM OF GENUS *NOVOSPHINGOBIUM***

(71) Applicant: Sumitomo Chemical Company, Limited, Tokyo (JP)

(72) Inventor: Tomokazu Mitsui, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 4 days.

(21) Appl. No.: 16/312,643

(22) PCT Filed: Jun. 27, 2017

(86) PCT No.: PCT/JP2017/023593
§ 371 (c)(1),
(2) Date: Dec. 21, 2018

(87) PCT Pub. No.: WO2018/003804
PCT Pub. Date: Jan. 4, 2018

(65) Prior Publication Data
US 2019/0256895 A1 Aug. 22, 2019

(30) Foreign Application Priority Data

Jun. 30, 2016 (JP) .............................. JP2016-129922

(51) Int. Cl.
*C07H 21/04* (2006.01)
*C12Q 1/68* (2018.01)
*C12Q 1/689* (2018.01)
*C12N 15/09* (2006.01)

(52) U.S. Cl.
CPC ............. *C12Q 1/689* (2013.01); *C12N 15/09* (2013.01)

(58) Field of Classification Search
None
See application file for complete search history.

(56) References Cited

U.S. PATENT DOCUMENTS

2018/0057858 A1 3/2018 Mitsui

FOREIGN PATENT DOCUMENTS

| CN | 104745709 A | * | 7/2015 |
| CN | 104745709 A | | 7/2015 |
| JP | 2004097934 A | | 4/2004 |
| JP | 2005254205 A | | 9/2005 |
| JP | 2015188359 A | | 11/2015 |
| JP | 2016195565 A | | 11/2016 |

OTHER PUBLICATIONS

NEB Random Primer 1998, p. 121-122.*
Rutebemberwa et al. (PLOS, vol. 9, No. 10,e111150, Oct. 2014) (Year: 2014).*
GenBank accession No. LN890294.1 (Year: 2015).*
Buck et al. (BioTechniques (1999) 27(3): 528-536) (Year: 1999).*
Lowe et al. (Nucleic Acids Research (1990) 18(7): 1757-1761). (Year: 1990).*
Database GenBank, [ online], Accession No. DQ831000, <https://www.ncbi.nlm.nih.gov/ nuccore/dq831000.1>, May 23, 2007 uploaded, Yan,Q.X. et al., Definition: *Novosphingobium* sp. FND-3 16S ribosomal RNA gene, partial sequence, 1 page.
Database GenBank, [ online], Accession No. EF029110, <https://www.ncbi.nlm.nih.gov/ nuccore/EF029110>, Sep. 25, 2012 uploaded, Lim, Y.W. et al., Definition: Novosphingobium resinovorum strain NCIMB 8767 16S ribosomal RNA gene, partial sequence, 1 page.
Database GenBank, [ online], Accession No. KF544921, <https://www.ncbi.nlm.nih.gov/ nuccore/kf544921>, Sep. 16, 2013 uploaded, Rodriguez,S. et al., Definition: *Novosphingobium* sp. S7 16S ribosomal RNA gene, partial sequence, 1 page.
Database GenBank, [ online], Accession No. KF544932, <https://www.ncbi.nlm.nih.gov/ nuccore/kf544932>, Sep. 16, 2013 uploaded, Rodriguez,S. et al., Definition: *Novosphingobium* sp. HS2a 16S ribosomal RNA gene, partial sequence, 1 page.
English Translation of International Search Report dated Sep. 12, 2017 in International Application No. PCT/JP2017/023593.
English Translation of Written Opinion dated Sep. 12, 2017 in International Application No. PCT/JP2017/023593.
Rutebemberwa et al., "Novosphingobium and Its Potential Role in Chronic Obstructive Pulmonary Diseases: Insights from Microbiome Studies," PLOS One, vol. 9, No. 10, e111150, pp. 1-13 (2014).
Zhou et al., "Development of genus-specific primers for better understanding the diversity and population structure of Sphingomonas in soils," Journal of Basic Microbiology, vol. 54, pp. 880-888 (2014).

* cited by examiner

*Primary Examiner* — Jeanine A Goldberg
(74) *Attorney, Agent, or Firm* — Panitch Schwarze Belisario & Nadel LLP; Stephany G. Small.; Sandra M. Katz

(57) ABSTRACT

A method for detecting a bacterium of the genus *Novosphingobium*, includes a first step of amplifying nucleotides using a test DNA as a template and primers capable of amplifying a nucleotide sequence of consecutive 94 or more nucleotides and 136 or less nucleotides in the nucleotide sequence of SEQ ID NO: 1 to obtain an amplified product; and a second step of detecting the amplified product.

1 Claim, No Drawings
Specification includes a Sequence Listing.

SEQUENCE LISTING

<160> NUMBER OF SEQ ID NOS: 9

<210> SEQ ID NO 1
<211> LENGTH: 136
<212> TYPE: DNA
<213> ORGANISM: Novosphingobium

<400> SEQUENCE: 1
cccggaactg cctttgaaac taggtgacta gaatcttgga gaggtcagtg gaattccgag      60
tgtagaggtg aaattcgtag atattcggaa gaacaccagt ggcgaaggcg actgactgga     120
caagtattga cgctga                                                    136

<210> SEQ ID NO 2
<211> LENGTH: 22
<212> TYPE: DNA
<213> ORGANISM: Artificial Sequence
<220> FEATURE:
<223> OTHER INFORMATION: synthetic

<400> SEQUENCE: 2
cccggaactg cctttgaaac ta                                              22

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
tcagcgtcar tacttgtcca gtca                                            24

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
tccgagtgta gaggtgaaat                                                 20

<210> SEQ ID NO 5
<211> LENGTH: 20

```
<212> TYPE: DNA
<213> ORGANISM: Artificial Sequence
<220> FEATURE:
<223> OTHER INFORMATION: synthetic

<400> SEQUENCE: 5
cgtcaatact tgtccagtca                                                  20

<210> SEQ ID NO 6
<211> LENGTH: 1411
<212> TYPE: DNA
<213> ORGANISM: Novosphingobium sp.NITE BP-02266

<400> SEQUENCE: 6
aacgaacgct ggcggcatgc ctaacacatg caagtcgaac gagatcttcg gatctagtgg      60
cgcacgggtg cgtaacgcgt gggaatctgc ccttgggttc ggaataacag tgagaaatta     120
ctgctaatac cggatgatgt cttcggacca agatttatc gcccagggat gagcccgcgt      180
aggattaggt agttggtggg gtaatggcct accaagccga cgatccttag ctggtctgag     240
aggatgatca gccacactgg gactgagaca cggcccagac tcctacggga ggcagcagtg    300
gggaatattg gacaatgggc gaaagcctga tccagcaatg ccgcgtgagt gatgaaggcc   360
ttagggttgt aaagctcttt taccagggat gataatgaca gtacctggag aataagctcc   420
ggctaactcc gtgccagcag ccgcggtaat acggagggag ctagcgttgt tcggaattac   480
tgggcgtaaa gcgcgcgtag gcggttactc aagtcagagg tgaaagcccg ggctcaacc    540 ccggaactgc cttgaaact aggtgactag aatcttggag aggtcagtgg aattccgagt    600
gtagaggtga aattcgtaga tattcggaag aacaccagtg gcgaaggcga ctgactggac   660
aagtattgac gctgaggtgc gaaagcgtgg ggagcaaaca ggattagata ccctggtagt  720
ccacgccgta aacgatgata actagctgtc cgggtacttg gtacttgggt ggcgcagcta   780
acgcattaag ttatccgcct ggggagtacg gtcgcaagat taaaactcaa aggaattgac   840
gggggcctgc acaagcggtg gagcatgtgg tttaattcga agcaacgcgc agaaccttac   900
cagcgtttga catgccggtc gcggatttgg gagaccattt ccttcagttc ggctggaccg   960
tgcacaggtg ctgcatggct gtcgtcagct cgtgtcgtga tgttgggt taagtcccgc    1020 aacgagcgca accctcgtcc ttagttgcca gcatttagtt gggcactcta aggaaactgc   1080
cggtgataag ccggaggaag gtggggatga cgtcaagtcc tcatggccct tacacgctgg  1140
gctacacacg tgctacaatg gcggtgacag tgggcagcaa gcacgcgagt gtgagctaat  1200
ctccaaaagc cgtctcagtt cggattgttc tctgcaactc gagagcatga aggcggaatc  1260
gctagtaatc gcggatcagc atgccgcggt gaatacgttc ccaggccttg tacacaccgc  1320
ccgtcacacc atgggagttg gattcactcg aaggcgttga gctaacccgc aagggaggca  1380
ggcgaccaca gtgggtttag cgactggggt g                                  1411

<210> SEQ ID NO 7
<211> LENGTH: 1409
<212> TYPE: DNA
<213> ORGANISM: Novosphingobium sp.NITE BP-02267

<400> SEQUENCE: 7
aacgaacgct ggcggcatgc ctaacacatg caagtcgaac gagaccttcg ggtctagtgg    60
cgcacgggtg cgtaacgcgt gggaatctgc cccttggttc ggaataacac agagaaattt  120
gtgctaatac cggatgatga cttcggtcca agatttatc gccgagggat gagcccgcgt    180
```

```
aggattaggt agttggtggg gtaatggcct accaagccga cgatccttag ctggtctgag    240
aggatgatca gccacactgg gactgagaca cggcccagac tcctacggga ggcagcagtg    300
gggaatattg gacaatgggc gaaagcctga tccagcaatg ccgcgtgagt gatgaaggcc    360
ttagggttgt aaagctcttt tacccgggat gataatgaca gtaccgggag aataagctcc    420
ggctaactcc gtgccagcag ccgcggtaat acggagggag ctagcgttgt tcggaattac    480
tgggcgtaaa gcgcgcgtag gcggttactc aagtcagagg tgaaagcccg gggctcaacc    540
ccggaactgc ctttgaaact aggtgactag aatcttggag aggtcagtgg aattccgagt    600
gtagaggtga aattcgtaga tattcggaag aacaccagtg gcgaaggcga ctgactggac    660
aagtattgac gctgaggtgc gaaagcgtgg ggagcaaaca ggattagata ccctggtagt    720
ccacgccgta aacgatgata actagctgtc cgggcacatg gtgtttgggt ggcgcagcta    780
acgcattaag ttatccgcct ggggagtacg gtcgcaagat taaaactcaa aggaattgac    840
gggggcctgc acaagcggtg gagcatgtgg tttaattcga agcaacgcgc agaaccttac    900
cagcgtttga catcctcatc gcgatttcca gagatggatt tcttcagttc ggctggatga    960
gtgacaggtg ctgcatggct gtcgtcagct cgtgtcgtga gatgttgggt taagtcccgc   1020
aacgagcgca accctcgtcc ttagttgcca tcatttagtt gggcactcta aggaaactgc   1080
cggtgataag ccggaggaag gtggggatga cgtcaagtcc tcatggccct tacacgctgg   1140
gctacacacg tgctacaatg gcggtgacag tgggcagcaa gcacgcgagt gtgagctaat   1200
ctccaaaagc cgtctcagtt cggattgcac tctgcaactc gagtgcatga aggcggaatc   1260
gctagtaatc gcggatcagc atgccgcggt gaatacgttc ccaggccttg tacacaccgc   1320
ccgtcacacc atgggagttg gtttcacccg aaggcagtgc gctaaccgca aggaggcagc   1380
tgaccacggt gggatcagcg actggggtg                                     1409
```

```
<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
agrgtttgat cmtggctcag                                                  20

<210> SEQ ID NO 9
<211> LENGTH: 19
<212> TYPE: DNA
<213> ORGANISM: Artificial Sequence
<220> FEATURE:
<223> OTHER INFORMATION: synthetic

<400> SEQUENCE: 9
ggytaccttg ttacgactt                                                   19
```

METHOD AND KIT FOR DETECTING BACTERIUM OF GENUS NOVOSPHINGOBIUM

CROSS-REFERENCE TO RELATED APPLICATION

This application is a Section 371 of International Application No. PCT/JP2017/023593, filed Jun. 27, 2017, which was published in the Japanese language on Jan. 4, 2018 under International Publication No. WO 2018/003804 A1, which claims priority under 35 U.S.C. § 119(b) to Japanese Application No. 2016-129922, filed Jun. 30, 2016, and the disclosures of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "S415760001 Sequence Listing", creation date of Jun. 26, 2017, and having a size of about 5.6 KB. The sequence listing submitted via EFS-Web is part of the specification and is herein incorporated by reference in its entirety.

TECHNICAL FIELD

The present invention relates to a method and a kit for detecting a bacterium of the genus *Novosphingobium*.

BACKGROUND ART

Activated sludge used in a drainage treatment contains a variety of kinds of microorganisms, and among such microorganisms, bacteria of the genus *Novosphingobium* are known to contribute to decomposition of oil including monocyclic aromatic hydrocarbons and polycyclic aromatic hydrocarbons (Patent document 1). In the drainage treatment, it is desired to monitor and regulate the amount of bacteria of the genus *Novosphingobium* in activated sludge according to the amount of oil in the drainage and the treatment speed required for the drainage treatment. To that end, it is a problem to rapidly detect only bacteria of the genus *Novosphingobium* in the activated sludge in which a plurality of species of microorganisms are present.

Non Patent Literature 1 reports predetermined primers for detecting a bacterium of the genus *Novosphingobium*.

PRIOR ART DOCUMENTS

Patent Document

Patent Document 1: JP-A-2004-97934

Non-Patent Document

Non-Patent Document 1: Rutebemberwa A et al., PLoS One. 2014 Oct. 23; 9(10):e111150.

SUMMARY OF THE INVENTION

Problems to be Solved by the Invention

The present inventors attempted to detect a bacterium of the genus *Novosphingobium* from activated sludge with the primers described in Non-Patent Document 1, and found that a bacterium of the genus *Novosphingobium* cannot be necessarily detected in a specific manner. When such a problem arises, the quantitativity of a bacterium of the genus *Novosphingobium* is not necessarily sufficient, and it becomes difficult to control reactions for removing oil in the drainage.

In view of the aforementioned circumstances, an object of the present invention is to provide a method for detecting a bacterium of the genus *Novosphingobium*, the method being capable of specifically detecting the bacterium of the genus *Novosphingobium* even in a system where a plurality of species of microorganisms are present, and a kit to be used for the method.

Means for Solving the Problems

The present invention is based on the new finding that a specific region of a 16S rRNA gene of a bacterium of the genus *Novosphingobium* existing in activated sludge is useful for specifically detecting a bacterium of the genus *Novosphingobium* in a system where a plurality of species of microorganisms are present.

The present invention relates to the following [1] to [5]:

[1] A method for detecting a bacterium of the genus *Novosphingobium*, comprising:

a first step of amplifying nucleotides using a test DNA as a template and primers capable of amplifying a nucleotide sequence of consecutive 94 or more nucleotides and 136 or less nucleotides in the nucleotide sequence of SEQ ID NO: 1 to obtain an amplified product; and a second step of detecting the amplified product.

[2] The method according to [1], wherein the primers used in the first step are a first primer comprising a nucleotide sequence having 2 or less nucleotides different from the nucleotide sequence of SEQ ID NO: 2, and a second primer comprising a nucleotide sequence having 2 or less nucleotides different from the nucleotide sequence of SEQ ID NO: 3.

[3] The method according to [1] or [2], wherein the primers used in the first step are a first primer comprising the nucleotide sequence of SEQ ID NO: 2, and a second primer comprising the nucleotide sequence of SEQ ID NO: 3.

[4] A kit to be used for detecting a bacterium of the genus *Novosphingobium*, comprising a primer set including: a first primer comprising a nucleotide sequence having 2 or less nucleotides different from the nucleotide sequence of SEQ ID NO: 2, and a second primer comprising a nucleotide sequence having 2 or less nucleotides different from the nucleotide sequence of SEQ ID NO: 3.

[5] The kit according to [4], wherein the first primer is a primer comprising the nucleotide sequence of SEQ ID NO: 2, and the second primer is a primer comprising the nucleotide sequence of SEQ ID NO: 3.

Effect of the Invention

According to the present invention, it is possible to provide a method for detecting a bacterium of the genus *Novosphingobium*, the method being capable of specifically detecting the bacterium of the genus *Novosphingobium* even in a system where a plurality of species of microorganisms are present and a kit to be used for the method.

MODE FOR CARRYING OUT THE INVENTION

A mode for carrying out the present invention (hereinafter, referred to as the "the present embodiment") is described in detail below. The present invention is not limited to the following embodiment.

Description of General Terms

Hereinafter, the terms generally used in the present description have the following meanings unless otherwise specified. *Novosphingobium* sp. NITE BP-02266 means a bacterium strain deposited as *Novosphingobium* sp. (Receipt number: NITE BP-02266, Date of the original deposit: May 26, 2016) to National Institute of Technology and Evaluation, Patent Microorganisms Depositary (NPMD, Address: #122, 2-5-8 Kazusakamatari, Kisarazu, Chiba 292-0818, Japan) by virtue of the Budapest Treaty.

*Novosphingobium* sp. NITE BP-02267 means a bacterium strain deposited as *Novosphingobium* sp. (Receipt number: NITE BP-02267, Date of the original deposit: May 26, 2016) to National Institute of Technology and Evaluation, Patent Microorganisms Depositary (NPMD, Address: #122, 2-5-8 Kazusakamatari, Kisarazu, Chiba 292-0818, Japan) by virtue of the Budapest Treaty.

<Method for Detecting Bacterium of Genus *Novosphingobium*>

A method for detecting a bacterium of the genus *Novosphingobium* of the present embodiment comprises:

a first step of amplifying nucleotides using a test DNA as a template and primers capable of amplifying a nucleotide sequence of consecutive 94 or more nucleotides and 136 or less nucleotides in the nucleotide sequence of SEQ ID NO: 1 to obtain an amplified product; and a second step of detecting the amplified product.

If an amplified product is obtained from the test DNA in the first step and it was possible to detect the amplified product in the second step, it can be determined that the DNA derived from a bacterium of the genus *Novosphingobium* is contained in the test DNA.

The bacterium of the genus *Novosphingobium* that is specifically detected by the detection method of the present invention may be quantified.

For example, by quantifying the bacterium of the genus *Novosphingobium* in activated sludge in the drainage treatment, it is possible to control reactions for removing oil in the drainage on the basis of the obtained detection amount of the bacterium of the genus *Novosphingobium*.

[First Step]

Examples of the test DNA according to the present embodiment include plasmid DNA, cDNA, and genomic DNA. The test DNA may comprise DNAs derived from a plurality of species of microorganisms, or DNA prepared from activated sludge. As the test DNA, DNA prepared from activated sludge is preferred from the viewpoint of controlling reactions for removing oil in the drainage. As a method for preparing the test DNA, a method well known to those skilled in the art may be used. As a method for preparing DNA from activated sludge, for example, commercially available DNA extraction kits may be used.

SEQ ID NO: 1 sets forth the nucleotide sequence of the positions 540 to 675 of SEQ ID NO: 6. SEQ ID NO: 6 sets forth a nucleotide sequence of a 16S rRNA gene of a bacterium of the genus *Novosphingobium*. In the 16S rRNA gene, there are a conserved region containing a sequence common to species and 9 variable regions (V1 to V9) containing sequences that vary depending on the species or the genus on the gene. In the nucleotide sequence of SEQ ID NO: 6, the nucleotide sequence of the positions 506 to 567 is the V4 region, and the nucleotide sequence of the positions 568 to 745 is the conserved region.

The nucleotide sequence of SEQ ID NO: 1 is a nucleotide sequence of a region containing a part of the V4 region and a part of the conserved region of the 16S rRNA gene.

In the first step according to the present embodiment, the amplified product is prepared by amplifying nucleotides using primers capable of amplifying a nucleotide sequence of consecutive 94 or more nucleotides and 136 or less nucleotides in the nucleotide sequence of SEQ ID NO: 1.

The amplified product may be prepared by amplifying nucleotides using primers capable of amplifying a nucleotide sequence of consecutive 110 or more nucleotides and 136 or less nucleotides or may be prepared by amplifying nucleotides using primers capable of amplifying a nucleotide sequence of consecutive 120 or more nucleotides and 136 or less nucleotides. The amplified product may be, for example, a nucleotide sequence having 1 to 6 nucleotides different from the correspondent region in the nucleotide sequence of SEQ ID NO: 1, or a nucleotide sequence having the same nucleotides as the correspondent region in the nucleotide sequence of SEQ ID NO: 1 as long as the amplified product is prepared by the amplification using such primers. By using the amplified product including the nucleotide sequence described above, it is possible to specifically detect a bacterium of the genus *Novosphingobium* in the subsequent second step.

The method for amplifying nucleotides to obtain an amplified product in the first step is not particularly limited, but a method well-known to those skilled in the art may be used. Examples of such a method include polymerase chain reaction (PCR), real-time PCR, and LAMP. Among these methods, real-time PCR is preferred since, at the same time as the amplification, the detection in the second step can be conducted and the amplified product can be quantified.

The primers used in the first step can be designed to be capable of amplifying a region containing a part of the V4 region and a part of the conserved region of the 16S rRNA gene of a bacterium of the genus *Novosphingobium*. Examples of the primers include a first primer (forward primer) that hybridizes with the antisense strand of the DNA encoding 16S rRNA under stringent conditions and a second primer (reverse primer) that hybridizes with the sense strand of the DNA encoding 16S rRNA under stringent conditions.

As used herein, "stringent conditions" means conditions under which a complementary strand of a nucleotide chain having a homology with a target sequence preferentially hybridizes with the target sequence and a complementary strand of a nucleotide chain not having such a homology substantially fails to hybridize with the target sequence. Stringent conditions are sequence-dependent and vary in a variety of situations. Longer sequences specifically hybridize at higher temperatures. In general, stringent conditions are selected so that the temperature is about 5° C. lower than the thermal melting temperature (Tm) of the particular sequence at the prescribed ionic strength and pH. Tm is a temperature at which 50% of nucleotides complementary to the target sequence hybridize with the target sequence in equilibrium under the prescribed ionic strength, pH, and DNA concentration.

The "primer comprising a nucleotide sequence that hybridizes under stringent conditions" may be, for example, a primer that hybridizes with a nucleotide of interest at high ion concentrations [for example, 6×SSC (900 mM sodium chloride, 90 mM sodium citrate) or the like is used.] at a temperature condition of 65° C. to form a DNA-DNA hybrid that is maintained even after washing for 30 minutes at low ion concentrations [for example, 0.1×SSC (15 mM sodium chloride, 1.5 mM sodium citrate) or the like is used.] at a temperature condition of 65° C.

The first primer and the second primer are not particularly limited as long as they are designed to be capable of amplifying nucleotides including a nucleotide sequence of consecutive 94 or more nucleotides and 136 or less nucleotides in the nucleotide sequence of SEQ ID NO: 1. The length of the primer is preferably 18 or more nucleotides, and more preferably 20 or more nucleotides from the view point of achieving more sufficient specificity. The upper limit of the length of the primer is preferably 30 or less nucleotides, and more preferably 25 or less nucleotides from the view point of increasing annealing efficiency.

Examples of the first primer that hybridizes with the antisense strand of the DNA encoding 16S rRNA under stringent conditions include a primer comprising a nucleotide sequence having 2 nucleotides different from a nucleotide sequence of consecutive 18 or more nucleotides in the nucleotide sequence of the DNA encoding 16S rRNA, preferably a primer comprising a nucleotide sequence having 1 nucleotide different from a nucleotide sequence of consecutive 18 or more nucleotides in the nucleotide sequence of the DNA encoding 16S rRNA, and more preferably a primer comprising a nucleotide sequence of consecutive 18 or more nucleotides in the nucleotide sequence of the DNA encoding 16S rRNA.

Examples of the first primer include a primer comprising a nucleotide sequence having 2 or less nucleotides different from the nucleotide sequence of SEQ ID NO: 2, preferably a primer comprising a nucleotide sequence having 1 or less nucleotide different from the nucleotide sequence of SEQ ID NO: 2, and more preferably a primer comprising the nucleotide sequence of SEQ ID NO: 2.

Examples of the second primer that hybridizes with the sense strand of the DNA encoding 16S rRNA under stringent conditions include a primer comprising a nucleotide sequence having 2 or less nucleotides different from a nucleotide sequence of consecutive 18 or more nucleotides in the nucleotide sequence complementary to the nucleotide sequence of the DNA encoding 16S rRNA, preferably a primer comprising a nucleotide sequence having 1 or less nucleotides different from a nucleotide sequence of consecutive 18 or more nucleotides in the nucleotide sequence complementary to the nucleotide sequence of the DNA encoding 16S rRNA, and more preferably a primer comprising a nucleotide sequence of consecutive 18 or more nucleotides in the nucleotide sequence complementary to the nucleotide sequence of the DNA encoding 16S rRNA.

Examples of the second primer include a primer comprising a nucleotide sequence having 2 or less nucleotides different from the nucleotide sequence of SEQ ID NO: 3, preferably a primer comprising a nucleotide sequence having 1 or less nucleotide different from the nucleotide sequence of SEQ ID NO: 3, and more preferably a primer comprising the nucleotide sequence of SEQ ID NO: 3.

[Second Step]

A method for detecting the amplified product in the second step is not particularly limited, but a method well-known to those skilled in the art may be used. Examples of the method for detecting the amplified product include agarose gel electrophoresis, real-time PCR, sequence analysis, and Southern blotting. Among these methods, detection methods using a probe are preferred from the view point of superior specificity. Examples of the detection methods using a probe include real-time PCR or Southern blotting and, among them, real-time PCR is preferred from the view point of being capable of conducting the amplification in the first step at the same time and specific detection and superior quantitativity.

The real-time PCR apparatus is not particularly limited, as long as it includes a thermal cycler that can amplify DNA by PCR and a spectrofluorometer for detecting the amplified product. Examples of the real-time PCR apparatus include StepOnePlus (manufactured by Applied Biosystems).

The amplified product detected in the second step may be quantified. Therefore, the detection method of the present embodiment not only detects a bacterium of the genus *Novosphingobium* from a test DNA but also enables quantification of the DNA derived from a bacterium of the genus *Novosphingobium* contained in the test DNA. For example, when real-time PCR is used for the detection of the amplified product in the second step, it is possible to quantify the amount of the test DNA from a calibration curve obtained using a standard sample. The calibration curve can be made based on Ct values indicating the number of cycles with which the amplified product reaches a certain value and the initial amounts of the template.

<Kit>

The kit to be used for detecting a bacterium of the genus *Novosphingobium* comprises a primer set including a first primer comprising a nucleotide sequence having 2 or less nucleotides different from the nucleotide sequence of SEQ ID NO: 2, and a second primer comprising a nucleotide sequence having 2 or less nucleotides different from the nucleotide sequence of SEQ ID NO: 3.

As the first primer and the second primer, those similar to the primers used in the aforementioned detection method may be used. The primer set made up of the first primer and the second primer is a primer set capable of detecting a bacterium of the genus *Novosphingobium*.

The kit of the present embodiment may include other reagents or the like as needed besides the primer set made up of the first primer and the second primer. Examples of the other reagents include a DNA polymerase, a deoxyribonucleotide mixture (dNTP Mix), $MgCl_2$, a buffer solution, sterilized water, and DNA for control. Although the concentration ranges of the other reagents or the like are not particularly limited as long as they are the concentration ranges capable of amplifying nucleotides and providing an amplified product, for example, the range may be 0.01 U/µL to 0.1 U/µL for the DNA polymerase, the range may be 100 µM to 500 µM for the deoxyribonucleotide mixture (dNTP Mix), and the range may be 1 mM to 5 mM for $MgCl_2$.

When a buffer solution is contained in the kit of the present embodiment, examples of the buffer solution include buffer solutions that are used in common PCR.

EXAMPLES

Example 1: Quantification Test Using Plasmid DNA Containing 16S rRNA Gene Derived from Bacterium of Genus *Novosphingobium*

(Materials)

Primers were designed so as to amplify the 16S rRNA gene derived from a bacterium of the genus *Novosphingobium*. Table 1 shows primers for amplifying the region of 16S rRNA set forth in SEQ ID NO: 1. As a template DNA, DNA of a plasmid into which the nucleotide sequence (SEQ ID NO: 6) of the 16S rRNA gene derived from *Novosphingobium* sp. NITE BP-02266 shown in Table 2 had been introduced was used. The plasmid used as the template DNA was obtained by preparing an amplified product by PCR using primers respectively having the nucleotide sequences of SEQ ID NOs: 8 and 9 and DNA extracted from *Novosphingobium* sp. NITE BP-02266 as a template and then introducing the amplified product into a plasmid. The PCR reaction was conducted: (1) at 94° C., for 2 minutes, (2) at 98° C., for 10 seconds, (3) at 60° C. for 30 seconds, and (4) at 68° C., for 1.5 minutes and the steps of (2) to (4) were repeated for 35 cycles.

TABLE 1

| Primer | Sequence (5'→3') | SEQ ID NO: |
|---|---|---|
| Forward primer | CCCGGAACTGCCTTTGAAACTA | 2 |
| Reverse primer | TCAGCGTCARTACTTGTCCAGTCA | 3 |

(Method)

Using the primers set forth in Tables 1, the 16S rRNA gene of a bacterium of the genus *Novosphingobium* was amplified with a real-time PCR apparatus (StepOnePlus, manufactured by Applied Biosystems).

10 µL of 2×SybrMaster Mix (manufactured by Life technologies), 0.20 µL of a forward primer (50 pmol/µL), 0.20 µL of a reverse primer (50 pmol/µL), 7.60 µL of sterilized water, and 2.00 µL of template DNA were added to a microtube and mixed. The microtube was placed in the real-time PCR apparatus and the amplification reaction was conducted. The amplification reaction was conducted (1) at 95° C., for 600 seconds, (2) at 95° C., for 15 seconds, and (3) at 60° C., for 60 seconds and the steps (2) and (3) were repeated for 40 cycles.

The progress of the reaction was observed in real time by irradiation with excitation light at 494 nm and measurement of fluorescence (521 nm) of the fluorescent substance SybrGreen.

(Result)

The primers set forth in Table 1 succeeded in detecting the plasmid DNA into which the nucleotide sequence (SEQ ID NO: 6) of the 16S rRNA gene derived from *Novosphingobium* sp. NITE BP-02266 has been introduced in a range of 1 pg/µL to 0.001 pg/µL.

Example 2: Specificity Test with One Kind of Plasmid DNA (Materials)

Primers set forth in Table 1.

A plasmid into which the nucleotide sequence (SEQ ID NO: 6) of the 16S rRNA gene derived from *Novosphingobium* sp. NITE BP-02266 has been introduced A plasmid into which the nucleotide sequence (SEQ ID NO: 7) of the 16S rRNA gene derived from *Novosphingobium* sp. NITE BP-02267 has been introduced Plasmid DNAs into which 16S rRNA genes derived from type strains of the bacteria set forth in Table 2 have been respectively introduced (Method)

Real-time PCR was conducted by a method similar to that in Example 1 except that any one of plasmid DNAs set forth in Table 2 was used as a template DNA.

(Result)

Table 2 illustrates the bacteria from which the 16S rRNA genes introduced into the plasmid DNAs used for the test are derived and the results of detection of these plasmid DNAs. By using the primers set forth in Table 1, it was possible to detect a plasmid DNA into which the 16S rRNA gene derived from the bacterium of the genus *Novosphingobium* has been introduced. On the other hand, plasmid DNAs into each of which 16S rRNA gene derived from a bacterium other than *Novosphingobium* bacteria has been introduced were below the detection limit (0.001 pg/µL). Therefore, it was revealed that the primers set forth in Table 1 are capable of specifically detecting a bacterium of the genus *Novosphingobium*.

TABLE 2

| Bacterial genus and species from which 16S rRNA gene is derived | Theoretical value of plasmid DNA (pg/µL) | Detection result of plasmid DNA |
|---|---|---|
| *Novosphingobium* sp. NITE BP-02266 | 1 | Detectable |
| *Novosphingobium* sp. NITE BP-02267 | 1 | Detectable |
| *Novosphingobium aquiterrae* | 1 | Detectable |
| *Novosphingobium lentum* | 1 | Detectable |
| *Novosphingobium naphthalenivorans* | 1 | Detectable |
| *Novosphingobium sediminis* | 1 | Detectable |
| *Novosphingobium tardaugens* | 1 | Detectable |
| *Sphingobium abikonense* | 1 | Below detection limit |
| *Sphingobium amiense* | 1 | Below detection limit |
| *Sphingobium cloacae* | 1 | Below detection limit |
| *Sphingobium xenophagum* | 1 | Below detection limit |
| *Sphingomonas herbicidovorans* | 1 | Below detection limit |
| *Sphingomonas adhaesiva* | 1 | Below detection limit |
| *Sphingomonas paucimobilis* | 1 | Below detection limit |
| *Sphingomonas rosa* | 1 | Below detection limit |

Example 3: Quantitativity Test with Mixed Plasmid DNAs of Plurality of Kinds (Materials)

Primers set forth in Table 1.

A plasmid DNA into which the nucleotide sequence (SEQ ID NO: 6) of the 16S rRNA gene derived from *Novosphingobium* sp NITE BP-02266 has been introduced Plasmids DNAs into each of which the 16S rRNA gene derived from among various bacteria set forth in Table 3 has been introduced (Method)

To a mixture of plasmid DNAs (the final concentrations of the various kinds of plasmid DNAs were each 1 pg/µL) into which the 16S rRNA genes derived from eleven kinds of bacteria set forth in Table 3 other than the genus *Novosphingobium* have been respectively introduced, a plasmid DNA into which the 16S rRNA gene derived from *Novosphingobium* sp. NITE BP-02266 has been introduced was mixed so that the final concentration was 1.0 pg/µL, 0.10 pg/µL, 0.010 pg/µL or 0.0010 pg/µL to prepare four mixture solutions of plasmid DNAs. Real-time PCR was conducted by a method similar to that in Example 1 except that the prepared plasmid DNA mixture was used as a template DNA.

(Result)

Table 4 illustrates the measurements (pg/μL) of the plasmid DNAs into which the 16S rRNA gene derived from *Novosphingobium* sp. NITE BP-02266 has been introduced, quantified by real-time PCR. The primers set forth in Table 1 were capable of specifically detecting only the plasmid DNA derived from the genus *Novosphingobium* even when a mixture of the plasmid DNAs into each of which 16S rRNA gene derived from among a plurality of kinds of bacteria other than the genus *Novosphingobium* has been introduced, and the plasmid DNA into which the 16S rRNA gene derived from the bacterium of the genus *Novosphingobium* has been introduced was used as a template DNA, and were capable of performing quantification up to a concentration of 0.001 pg/μL.

TABLE 3

| Origin of 16S rRNA gene | Concentration of plasmid DNA (pg/uL) |
|---|---|
| *Sphingobium* | 1 |
| *Xanthobacter* | 1 |
| *Sediminibacterium* | 1 |
| *Rhodococcus* | 1 |
| *Methyloversatilis* | 1 |
| *Methylibium* | 1 |
| *Sphingomonas* | 1 |
| *Haliscomenobacter* | 1 |
| *Nitrobacter* | 1 |
| *Nitrosomonas* | 1 |
| *Thermomonas* | 1 |

TABLE 4

| Theoretical value of plasmid DNA (pg/μL) | 1.0 | 0.10 | 0.010 | 0.0010 |
|---|---|---|---|---|
| Actual measurement of plasmid DNA (pg/μL) | 1.0 | 0.18 | 0.021 | 0.0033 |

Example 4: Specificity Test with One Kind of Genomic DNA (Materials)

Primers set forth in Table 1.

A genomic DNA derived from *Novosphingobium* sp. NITE BP-02266

A genomic DNA derived from *Novosphingobium* sp. NITE BP-02267

Genomic DNAs derived from type strains of bacteria set forth in Table 5

(Method)

Real-time PCR was conducted by a method similar to that in Example 1 except that genomic DNAs (1 ng/μL) derived from bacteria set forth in Table 5 were respectively used as a template DNA.

(Result)

The result of quantification by real-time PCR, converted into a concentration of plasmid DNA containing the 16S rRNA gene having the nucleotide sequence of SEQ ID NO: 6 is shown in Table 5. By using the primers set forth in Table 1, it was possible to detect the genomic DNA of a bacterium of the genus *Novosphingobium* up to a concentration of 0.001 ng/μL. Meanwhile, genomic DNAs derived from the other bacteria were below the detection limit (0.001 ng/μL). Therefore, it was revealed that the primers set forth in Table 1 are capable of specifically detecting a bacterium of the genus *Novosphingobium* even when genomic DNA is used.

TABLE 5

| Bacterial genus and species from which genomic DNA is derived | Theoretical value of genomic DNA (ng/μL) | Measurement result of genomic DNA |
|---|---|---|
| *Novosphingobium* sp.NITE BP-02266 | 1 | Detectable |
| *Novosphingobium* sp.NITE BP-02267 | 1 | Detectable |
| *Novosphingobium aquiterrae* | 1 | Detectable |
| *Novosphingobium lentum* | 1 | Detectable |
| *Novosphingobium naphthalenivorans* | 1 | Detectable |
| *Novosphingobium sediminis* | 1 | Detectable |
| *Novosphingobium tardaugens* | 1 | Detectable |
| *Sphingobium abikonense* | 1 | Below detection limit |
| *Sphingobium amiense* | 1 | Below detection limit |
| *Sphingobium cloacae* | 1 | Below detection limit |
| *Sphingobium xenophagum* | 1 | Below detection limit |
| *Sphingomonas herbicidovorans* | 1 | Below detection limit |
| *Sphingomonas adhaesiva* | 1 | Below detection limit |
| *Sphingomonas parapaucimobilis* | 1 | Below detection limit |
| *Sphingomonas paucimobilis* | 1 | Below detection limit |
| *Sphingomonas rosa* | 1 | Below detection limit |

Example 5: Quantitativity Test with Mixed Genomic DNAs of Plurality of Kinds (Materials)

Primers set forth in Table 1.

A genomic DNA derived from *Novosphingobium* sp NITE BP-02266

Genomic DNAs derived from bacteria set forth in Table 6

(Method)

To a mixture (the final concentrations of the various kinds of plasmid DNAs were each 100 pg/μL) in which genomic DNAs derived from eleven kinds of bacteria other than the genus *Novosphingobium* among the bacteria set forth in Table 6 are mixed, a genomic DNA derived from *Novosphingobium* sp. NITE BP-02266 was mixed so that the final concentration was 100 pg/μL, 10 pg/μL, 1.0 pg/μL or 0.10 pg/μL to prepare four mixture solutions of genomic DNAs. Real-time PCR was conducted by a method similar to that in Example 1 except that the prepared genomic DNA mixture was used as a template DNA.

TABLE 6

| Bacterial genus and species from which genomic DNA is derived | Concentration of genomic DNA (pg/uL) |
|---|---|
| *Bacillus licheniformis* | 100 |
| *Bacillus subtilis* | 100 |
| *Rhizobium meliloti* | 100 |
| *Rhizobium leguminosarum* | 100 |
| *Escherichia coli* | 100 |
| *Bradyrhizobium diazoefficiens* | 100 |
| *Bradyrhizobium japonicum* | 100 |
| *Sphingomonas paucimobilis* | 100 |
| *Sphingobium cloacae* | 100 |
| *Rhodococcus rhodochrous* | 100 |
| *Nitrobacter winogradskyi* | 100 |

(Result)

Table 7 illustrates the result of quantification of the genomic DNA derived from *Novosphingobium* sp. NITE BP-02266 with the primers set forth in Table 1. The primers set forth in Table 1 were capable of specifically detecting only the genomic DNA derived from *Novosphingobium* sp. even when a mixture of genomic DNAs derived from a plurality of kinds of bacteria including bacteria other than the genus *Novosphingobium* and a bacterium of the genus *Novosphingobium* was used as a template DNA, and were capable of performing quantification up to a concentration of 0.1 pg/μL.

TABLE 7

| Theoretical value of genome (pg/μL) | 100 | 10 | 1.0 | 0.10 |
|---|---|---|---|---|
| Actual measurement (pg/μL) | 230 | 29 | 1.7 | 0.19 |

Example 6: Detection of Bacterium of Genus *Novosphingobium* in Activated Sludge (Materials)

Primers set forth in Table 1.

Genomic DNA extracted from Activated sludge sample 1

(Method)

An amplified product was prepared by the PCR reaction using the primers set forth in Table 1, and genomic DNA (2 μL) derived from Activated sludge sample 1 as a template DNA, and the amplified product was introduced into a plasmid and then the nucleotide sequence of the amplified product was decoded. The decoded nucleotide sequence was looked up in the database (RDP) and a bacterial genus from which the decoded nucleotide sequence is derived was identified.

The PCR reaction was conducted: (1) at 94° C., for 2 minutes, (2) at 98° C., for 10 seconds, (3) at 60° C. for 30 seconds, and (4) at 68° C., for 30 seconds and the steps of (2) to (4) were repeated for 35 cycles.

(Result)

Table 8 illustrates bacteria that were detected with the primers set forth in Table 1, from the genomic DNA mixture derived from Activated sludge sample 1. A total of twelve sequences including four kinds of sequences were obtained, and every sequence was a sequence derived from a bacterium of the genus *Novosphingobium*. This result reveals that use of the primers set forth in Table 1 makes it possible to specifically amplifying a genomic DNA of a bacterium of the genus *Novosphingobium* directly from a genomic DNA mixture derived from activated sludge, and makes it possible to specifically detect the bacterium of the genus *Novosphingobium*.

TABLE 8

| Sample for detection | Detection rate | Detected genus |
|---|---|---|
| Activated sludge sample 1 Genomic DNA extract | 4/12 | *Novosphingobium* |
| | 5/12 | *Novosphingobium* |
| | 2/12 | *Novosphingobium* |
| | 1/12 | *Novosphingobium* |

Comparative Example 1: Specificity Test with One Kind of Plasmid DNA

Table 9 illustrates primers for detecting a bacterium of the genus *Novosphingobium* set forth in Non-Patent Document 1.

TABLE 9

| Primer | Sequence (5'→3') | SEQ ID NO: |
|---|---|---|
| Forward primer | TCCGAGTGTAGAGGTGAAAT | 4 |
| Reverse primer | CGTCAATACTTGTCCAGTCA | 5 |

(Materials)

Primers set forth in Table 9.

Plasmid DNAs into which 16S rRNA genes derived from bacteria set forth in Table 10 have been respectively introduced (Method)

Real-time PCR was conducted by a method similar to that in Example 2 except that the aforementioned primers were used and that any one kind of the plasmid DNAs set forth in Table 10 was used as a template DNA.

(Result)

Table 10 illustrates the bacteria from which the 16S rRNA genes introduced into the plasmid DNAs used for the test are derived and the results of detection of these plasmid DNAs. The primers set forth in Table 9 detected a part of a plasmid DNA into which a 16S rRNA gene derived from a bacterium other than *Novosphingobium* bacteria has been introduced, in addition to a plasmid DNA into which a 16S rRNA gene derived from a bacterium of the genus *Novosphingobium* has been introduced. Therefore, it was revealed that the primers set forth in Table 9 are not necessary capable of specifically detecting a bacterium of the genus *Novosphingobium*.

TABLE 10

| Bacterial genus and species from which 16SrRNA is derived | Theoretical value of plasmid DNA (ng/μL) | Detection result of plasmid DNA |
|---|---|---|
| *Novosphingobium* sp.NITE BP-02266 | 1 | Detectable |
| *Novosphingobium* sp.NITE BP-02267 | 1 | Detectable |
| *Novosphingobium aquiterrae* | 1 | Detectable |
| *Novosphingobium lentum* | 1 | Detectable |
| *Novosphingobium naphthalenivorans* | 1 | Detectable |
| *Novosphingobium sediminis* | 1 | Detectable |
| *Novosphingobium tardaugens* | 1 | Detectable |
| *Sphingobium abikonense* | 1 | Below detection limit |
| *Sphingobium amiense* | 1 | Detectable |
| *Sphingobium cloacae* | 1 | Below detection limit |
| *Sphingobium xenophagum* | 1 | Below detection limit |
| *Sphingomonas herbicidovorans* | 1 | Below detection limit |
| *Sphingomonas adhaesiva* | 1 | Detectable |
| *Sphingomonas paucimobilis* | 1 | Below detection limit |
| *Sphingomcas rosa* | 1 | Below detection limit |

Comparative Example 2: Detection of Bacterium of Genus *Novosphingobium* in Activated Sludge (Materials)
Primers set forth in Table 9.
DNA extracted from Activated sludge sample 1
(Method)
The bacterial genus from which the decoded nucleotide sequence is derived was identified by a method similar to that in Example 6 except that the aforementioned primers were used.
(Result)
Table 11 illustrates bacteria that were detected with the primers set forth in Table 9, from the genomic DNA derived from Activated sludge sample 1. A total of nine sequences including eight kinds of sequences were obtained. Eight sequences among the obtained nine sequences were sequences of other than *Novosphingobium* bacteria or sequences for which determination as a bacterium of the genus *Novosphingobium* cannot be made. This result revealed that the primers set forth in Table 9 are not necessarily capable of specifically detecting a bacterium of the genus *Novosphingobium* from a genomic DNA mixture derived from activated sludge.

TABLE 11

| Sample for detection | Detection rate | Detected genus |
|---|---|---|
| Activated sludge sample 1 | 2/9 | *Sphingomonadales* |
| Genomic DNA mixture | 1/9 | *Sphingopyxis* |
|  | 1/9 | Sphingomonadaceae |
|  | 1/9 | Sphingomonadaceae |
|  | 1/9 | Sphingomonadaceae |
|  | 1/9 | Sphingomonadaceae |
|  | 1/9 | *Novosphingobium* |
|  | 1/9 | *Alphaproteobacteria* |

The invention claimed is:

1. A method for detecting a bacterium of the genus *Novosphingobium*, comprising:
    a first step of amplifying nucleotides using a test DNA as a template and primers capable of amplifying a nucleotide sequence of consecutive 94 or more nucleotides and 136 or less nucleotides in the nucleotide sequence of SEQ ID NO: 1 to obtain an amplified product; and
    a second step of detecting the amplified product;
    wherein the test DNA is DNA prepared from activated sludge, and
    wherein the primers used in the first step are a first primer consisting of the nucleotide sequence of SEQ ID NO: 2, and a second primer consisting of the nucleotide sequence of SEQ ID NO: 3.

* * * * *